(12) United States Patent
Hosoya

(10) Patent No.: US 8,465,669 B2
(45) Date of Patent: Jun. 18, 2013

(54) MONOLITH SEPARATION MEDIUM FOR CHROMATOGRAPHY AND PROCESS FOR PRODUCING THE SAME

(75) Inventor: Ken Hosoya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/197,747

(22) Filed: Aug. 3, 2011

(65) Prior Publication Data
US 2011/0284447 A1 Nov. 24, 2011

Related U.S. Application Data

(62) Division of application No. 12/160,706, filed as application No. PCT/JP2006/300518 on Jan. 17, 2006, now abandoned.

(51) Int. Cl.
| | |
|---|---|
| *C01B 31/16* | (2006.01) |
| *C09K 3/00* | (2006.01) |
| *G01N 30/02* | (2006.01) |
| *G01N 30/90* | (2006.01) |
| *G01N 1/22* | (2006.01) |
| *G01N 33/497* | (2006.01) |
| *G01N 37/00* | (2006.01) |
| *B32B 3/26* | (2006.01) |
| *C08G 18/00* | (2006.01) |
| *B29C 65/00* | (2006.01) |
| *B29C 44/34* | (2006.01) |
| *C08J 9/00* | (2006.01) |

(52) U.S. Cl.
USPC ...... 252/184; 73/19.02; 73/19.12; 428/304.4; 428/320.2; 428/321.1; 521/50; 521/155; 521/156; 521/159; 521/161; 264/41; 264/53

(58) Field of Classification Search
USPC ............... 252/184; 524/909, 916; 73/19.02, 73/19.12; 428/304.4, 320.2, 321.1; 521/50, 521/155, 156, 159, 161; 264/41, 53; 525/903
See application file for complete search history.

(56) References Cited

U.S. PATENT DOCUMENTS
| | | | |
|---|---|---|---|
| 4,265,745 A | * | 5/1981 | Kawaguchi et al. .......... 210/654 |
| 5,453,185 A | | 9/1995 | Frechet et al. |

FOREIGN PATENT DOCUMENTS
WO   WO-2004/070378 A1   8/2004

OTHER PUBLICATIONS

International Search Report for the Application No. PCT/JP2006/300518 mailed Mar. 7, 2006.
PSIS CIM (R) EPOXY disk 2001 BIA Separations (www.biaseparations.com/pr/251/322/specific-information).
Hosoya, Ken et al., "High-Performance Polymer-Based Monolithic Capillary Column", Analytical Chemistry, 2006, vol. 78, No. 16, pp. 5729-5735.

(Continued)

*Primary Examiner* — Patrick Ryan
*Assistant Examiner* — Aaron Greso
(74) *Attorney, Agent, or Firm* — Cheng Law Group, PLLC

(57) ABSTRACT

To obtain a non-particle-aggregation-type organic polymer monolith separation medium, there is provided a monolith separation medium comprising a skeletal phase and pores being continuous in the form of three-dimensional network, which skeletal phase on its surface has a functional group permitting introduction of a new functional group. The skeletal phase has a non-particle-aggregation-type co-continuous structure having an average diameter of submicron to micrometer size, and is constituted of an addition polymer from an epoxy compound of bi- or higher functionality and an amine compound of bi- or higher functionality. Further, the skeletal phase is enriched in organic matter and does not contain any carbon atoms derived from aromatic series.

11 Claims, 3 Drawing Sheets

OTHER PUBLICATIONS

Ishizuka. Norio et al.. "Monolithic Silica Columns for High-Efficiency Separations by High-Performance Liquid Chromatography", Journal of Chromatography A (2002), vol. 960, pp. 85-96.

Pflegerl, Karin et al., "Direct Synthesis of Peptides on Convective Interaction Media Monolithic Columns for Affinity Chromatography", Journal of Combinatorial Chemistry, 2002, vol. 4, No. 1, pp. 33-37.

Vlakh, E. et al., "Solid Phase Peptide Synthesis on Epoxy-Bearing Methacrylate Monoliths", Journal of Peptide Science, 2004, vol. 10, pp. 719-730.

* cited by examiner

Fig. 1
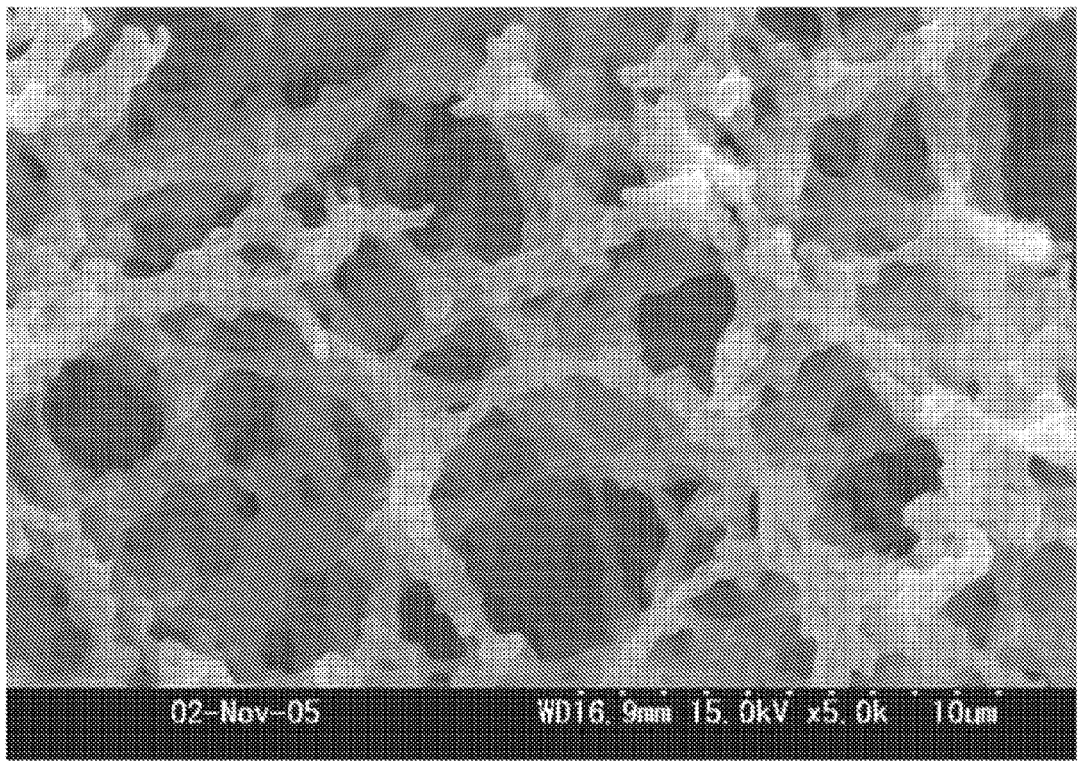
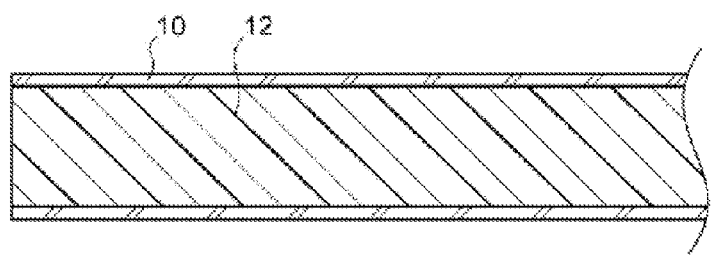

MONOLITH SEPARATION MEDIUM FOR CHROMATOGRAPHY AND PROCESS FOR PRODUCING THE SAME

CROSS-REFERENCE TO RELATED APPLICATIONS

The present application is a Divisional application of patent application Ser. No. 12/160,706, filed on Jul. 11, 2008 now abandoned, which is a 371 application of Application Serial No. PCT/JP2006/300518, filed Jan. 17, 2006, the entire contents of which are hereby incorporated into the present application by reference.

TECHNICAL FIELD

The present invention relates to a monolith separation medium for chromatography having a co-continuous structure comprising a skeletal phase enriched in an organic matter and a pore being continuous in the form of three-dimensional network, and to a process for producing the same.

BACKGROUND ART

It is reported about porous materials called monoliths in which through flow channels and a skeleton are integrated, that advantages which have not been recognized with conventional particle-filled type columns are developed, that is, when they are used as a separation medium for high-performance liquid chromatography, high column performance is obtained due to the wide flow channels and the thin skeleton, and deterioration of the performance is inhibited even under a high flow rate due to a low pressure loss (see N. Ishizuka, H. Kobayashi, H. Minakuchi, K. Nakanishi, K. Hirao, K. Hosoya, T. Ikegami and N. Tanaka, J. Chromatogr. A, 960, 85 (2002)).

Monoliths mainly comprising silica gel realize high performance due to their fine structural control, and some of them are commercially available.

While some polymer monoliths based on organic macromolecules are present, conventional polymer monoliths can not freeze the spinodal decomposition structure, which is a transitional state of a biphasic phase separation process, due to the heterogeneity of ordinary radical polymerization as mentioned later. Therefore, they are usually of particle aggregation type having more developed phase separation. Therefore, although a through pore is formed, the structure is of low uniformity and becomes particle aggregation type. As a result, high performance like that of monoliths based on silica gel has not been realized yet.

Conventionally, polymer monoliths are produced basically by combining hydrophobic monomer components such as styrene/divinylbenzene with, for example, a porogen which serves as a poor solvent for such monomers as represented by a patent to Svec, et al. (U.S. Pat. No. 5,453,185). In such a solution system, the van der Weals force between polymer chains is basically greater than the steric hindrance of growing polymer chains, resulting in flocculation of polymer chains. Thus, this causes generation of nuclei due to polymer chain entanglement, growth of microgel particles due to polymer chain flocculation, and rapid increase in surface energy of the system. Moreover, the microgel particles aggregate together, so that the gel continues similar growth (fractal) to get coarser. Therefore, such a system composed of a monomer and a poor solvent is characterized in that gel grows in the form of particle aggregation, and phase separation occurs extremely early in competition with gelation and a monolith form where macroporous pores have a small specific surface area is fixed, resulting in a particle aggregation type monolith. Therefore, conventional monoliths have no skeletal structure and inherently have some problems, such as large maze factors of a through pore, increase in back pressure at high flow rate, and morphological change due to monolith compressibility.

DISCLOSURE OF THE INVENTION

Problem to be Solved by the Invention

The present invention is made for solving the problems with the above-described conventional organic polymer monolith columns, and an object thereof is to provide a non-particle-aggregation-type organic polymer monolith, which serves as a separation medium, and a process for producing the same.

Means for Solving the Problem

As a result of extensive studies to solve such problems, it was found by the present inventors that a porous material having an extremely uniform skeletal structure can be obtained by dissolving an epoxy compound having a specific molecular structure in a porogen; adding an amine compound of bi- or higher functionality thereto and heating them to polymerize, thereby causing the resulting polymer and the porogen to undergo spinodal decomposition; crosslinking the materials stably before they transit to a particle-aggregation structure due to the growth of phase separation, thereby freezing a non-particle-aggregation-type co-continuous structure; and subsequently removing the porogen. It was also found that the resulting porous material can serve as a separation medium which develops an extremely high theoretical plate number due to the uniformity of the skeleton thereof. As a result, the present invention has been accomplished.

The organic macromolecular gel-like monolith separation medium for chromatography of the present invention comprises a skeletal phase, a pore which is formed by the skeletal phase and which is continuous in the form of three-dimensional network, and a functional group present on the surface of the skeletal phase and permitting introduction of a new functional group. The skeletal phase has an average diameter of submicron to micrometer size, and a non-particle-aggregation-type co-continuous structure. The skeletal phase is constituted of an addition polymer from an epoxy compound of bi- or higher functionality and an amine compound of bi- or higher functionality, enriched in an organic matter, and does not contain any carbon atom derived from aromatic series.

The functional group present on the surface of the skeletal phase and permitting introduction of a new functional group includes a hydroxyl group produced by a reaction between an epoxy group and an amino group, and an amino group or an epoxy group remaining unreacted.

A preferable example of the epoxy compound is 2,2,2-tri-(2,3-epoxypropyl)-isocyanurate. 2,2,2-Tri-(2,3-epoxypropyl)-isocyanurate is a chiral compound which includes optical antipodes. In the present invention, both a racemic mixture and an optically active substance can be used.

A chiral compound can be used also as the amine compound. Both a racemic mixture and an optically active substance can be used also as the amine compound.

Separation columns for high-performance liquid chromatography comprising the separation medium have 50,000 or more theoretical plates per meter of column length.

Separation media for optical resolution aiming at separation of the S-isomer and the R-isomer of optical antipodes by liquid chromatography are resultant monolithic separation media produced by the use of optically active substances as both an epoxy compound and an amine compound.

While optical resolution has conventionally been performed with optically activate polymers, polymers having an optically active site in their main chain are derived from "sugar", which is a natural product. Synthetic macromolecules cannot contain an optically active site in their main chain and therefore have a structure in which an optically active site is hung down from the main chain in the form of a pendant. In contrast, the polymer of the present invention in which optically active substances are used for both an epoxy compound and an amine compound contains an optically active site in its main chain despite being a synthetic macromolecule, and it therefore is an extremely rare separation medium. Moreover, it has a wide range of variations because it is possible to give an optically active site to monomer units of both the epoxy compound and the amine compound.

The production process of the present invention is a process for producing the monolith separation medium of the present invention. It has the following steps (A) to (C):

(A) a step of heating an epoxy compound of bi- or higher functionality and an amine compound of bi- or higher functionality within a range of from 60 to 200° C. in a porogen to polymerize them to obtain a gel-like material, (B) then a step of washing the gel-like material with a solvent such as water to remove the porogen to leave the skeletal phase, and (C) then a step of drying.

The polymerization temperature in the porogen is a temperature suitable for the epoxy compound and the amine compound to dissolve in the porogen and undergo a polymerization reaction. It may be set appropriately depending upon the types of the epoxy compound, the amine compound and the porogen.

A preferable example of the epoxy compound used in the production process is 2,2,2-tri-(2,3-epoxypropyl)-isocyanurate. This epoxy compound may be either a racemic mixture or an optically active substance.

The amine compound, which is a component to be used as a hardener, may be either a racemic mixture or an optically active substance, and examples thereof include an aliphatic amine such as ethylenediamine, diethylenetriamine, triethylenetetramine, tetraethylenepentamine, iminobispropylamine, bis(hexamethylene)triamine, 1,3,6-trisaminomethylhexane, polymethylenediamine, trimethylhexamethylenediamine and polyether diamine, an alicyclic polyamine such as isophoronediamine, menthanediamine, N-aminoethylpiperazine, 3,9-bis(3-aminopropyl)2,4,8,10-tetraoxaspiron, bis(4-aminocyclohexyl)methane and a modified product thereof, and an aliphatic polyamidoamines composed of a polyamine and a dimmer acid. What are preferred are alicyclic amine compounds having two or more primary amines in the molecule, and particularly preferred are bis(4-aminocyclohexyl)methane, bis(4-amino-3-methylcyclohexyl)methane and the like.

A porogen is a solvent which can dissolve an epoxy compound and a hardener and can produce a reaction-inducing phase separation after the polymerization of the epoxy compound and the hardener. Examples of the porogen include cellosolves such as methyl cellosolve and ethylcellosolve, esters such as ethylene glycol monomethyl ether acetate and propylene glycol monomethyl ether acetate, and glycols such as polyethylene glycol and polypropylene glycol. In particular, polyethylene glycol having a molecular weight of 600 or less is preferred, and especially, polyethylene glycol having a molecular weight of 300 or less is preferred.

In the production process of the present invention, when 2,2,2-tri-(2,3-epoxypropyl)-isocyanurate is used as the epoxy compound, the raw material formulation of the amine to the epoxy compound in molar ratio is suitably within an epoxy compound:amine range of from 1:1 to 1:3. The added amount of the porogen is suitably from 1 to 99% to the total weight of the epoxy compound, the amine and the porogen.

Effect of the Invention

The monolith separation medium of the present invention is useful as a stationary phase for liquid chromatography which demonstrates unprecedentedly high performance because the skeletal phase thereof has an average diameter of submicron to micrometer size, and has a non-particle-aggregation-type co-continuous structure, and is constituted of an addition polymer from an epoxy compound of bi- or higher functionality and an amine compound of bi- or higher functionality, and is enriched in an organic matter, and does not contain any carbon atoms derived from aromatic series. Moreover, it can be used for columns of general-purpose size as well as for capillary columns.

Columns for separation which are made of this separation medium can be configured to have a theoretical plate number of 50,000 or more per meter of column length.

When a monolith separation medium is formed using optically active substances as both the epoxy compound and the amine compound, it becomes possible to separate the S-isomer and the R-isomer of optical antipodes with this separation medium.

The production process of the present invention can be used effectively for columns having relatively large diameters as well as capillary columns because it is an extremely convenient technique in which an epoxy compound and an amine compound are heated in a porogen to polymerize.

BEST MODE FOR CARRYING OUT THE INVENTION

The separation medium of the present invention in which a non-particle-aggregation-type and high-performance polymer monolith is formed is produced from a specific combination of an epoxy compound and a hardener to be used as raw materials. Specifically, it is preferable that the epoxy compound is a non-aromatic epoxy compound of bi- or higher functionality and the hardener be a non-aromatic amine compound.

Among such Combinations, 2,2,2-tri-(2,3-epoxypropyl)-isocyanurate is preferred as the non-aromatic epoxy compound (e.g., TEPIC, which is a commercial name of Nissan Chemistry Industries, Ltd.). A combination thereof with an amine compound of bi- or higher functionality is preferable because it results in a high-performance polymer monolith separation medium with a non-particle-aggregation-type and three-dimensionally branched structure.

Hereinafter, examples of epoxy compounds and hardeners which can be used in the present invention are shown.

An epoxy compound provided as an example is 2,2,2-tri-(2,3-epoxypropyl)-isocyanurate, which may be either a racemic mixture or an optically active substance.

EXAMPLES

Next, examples of a separation medium and examples of a production process suitable for producing the separation medium efficiently are described.

Example 1

Reagents and Solvent

Used were 2,2,2-tri-(2,3-epoxypropyl)-isocyanurate (TEPIC-S), which is an optically active SSS-isomer, as epoxy compound, bis(4-aminocyclohexyl)methane (BACM) as an amine compound, and polyethylene glycol having a molecular weight of 200 (PEG200, a commercial name of Nacalai Tesque, Inc.) as a porogen.

The chemical structure formulas of TEPIC and BACM are shown below.

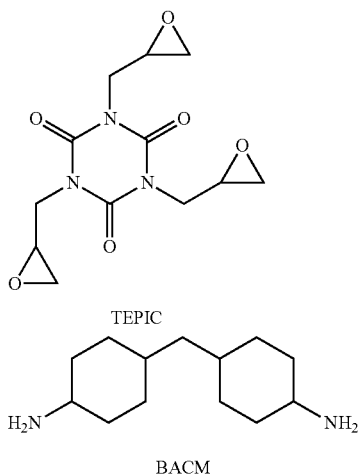

TEPIC

BACM

[Production of Polymer Monolith]

Following addition of 0.37 g of BACM and 7.00 g of PEG200 to 1.6 g of TEPIC-S, they were heated and stirred with a hot stirrer into a state where they are dissolved. Thereafter, they were filled into a fused quartz capillary tube 10 and heated for 20 hours in a drier at 80° C. to be polymerized.

Then, the resultant was washed with water and methanol, and then dried in vacuo.

Production Conditions

| | |
|---|---|
| TEPIC-S | 1.6 g |
| BACM | 0.37 g |
| PEG200 | 7.00 g |
| Temperature | 80° C. |

A scanning electron micrograph of the monolith separation medium 12 in the organic polymer monolith capillary column produced by the above-described polymerization is shown in FIG. 1. It is shown that the skeletal phase of this monolith has an average diameter of submicron size and has a non-particle-aggregation-type co-continuous structure, and that a pore formed by the skeletal phase has a three-dimensional network.

A separation chromatogram of uracil and alkylbenzenes obtained by use of the organic polymer monolith capillary column (100 μm in inner diameter and 21.5 cm in length) of the present invention produced above is shown in FIG. 2. The alkylbenzenes range from benzene, whose substituent has zero carbon atoms, to hexylbenzene, whose substituent has six carbon atoms. The mobile phase was a 60% aqueous acetonitrile solution, which was adjusted to pH 7.0 with 20 mM phosphate buffer, and the column temperature was room temperature. The detection was conducted by ultraviolet absorption at 210 nm.

N in FIG. 2 denotes the theoretical plate number, and indicates, from the top, uracil, benzene and alkylbenzenes. The lower an alkylbenzene is placed, the more carbon atoms its substituent has.

The theoretical plate number was calculated by the half-value width method by use of the following equation.

$$N = 5.54(t_r/W_{0.5h})^2$$

Here, $t_r$ denotes a retention time and $W_{0.5h}$ denotes a half-value width.

The results show that a theoretical plate number (N) of 30,000 or more was obtained with a 21.5 cm long column for all the solutes. That is, the theoretical plate number is about 140,000 per meter.

Example 2

By using optically active substances as both an epoxy compound and an amine compound, a chiral organic polymer monolith capillary column was produced.

An optically active SSS-isomer of 2,2,2-tri-(2,3-epoxypropyl)-isocyanurate (TEPIC-S) in an amount of 0.40 g as an epoxy compound, 0.63 g of an optically active isomer, (1S, 2S)-(+)-1,2-cyclohexanediamine, and 10 g of polyethylene glycol having a molecular weight 300 (PEG300) were mixed, heated and stirred into a state where they were dissolved. Thereafter, they were filled into a fused quartz capillary tube, and heated for 4 hours in an oven at 120° C. to be polymerized.

Then, the resultant was washed with water and methanol, and then dried in vacuo.

Production Conditions

| | |
|---|---|
| TEPIC-S | 0.40 g |
| (1S,2S)-(+)-1,2-cyclohexanediamine | 0.63 g |
| PEG300 | 12.64 g |
| Temperature | 120° C. |

The organic polymer monolith of Example 2 produced by the above-mentioned polymerization was also a skeletal phase similar to that of the example 1.

A separation chromatogram of optical antipodes (R,S)-1, 1'-bis-2-naphtol obtained by use of the organic polymer monolith capillary column (100 μm in inner diameter and 17.5 cm in length) of the present invention produced above is shown in FIG. 3. The mobile phase was a 60% aqueous acetonitrile solution, which was adjusted to pH 7.0 with 20 mM phosphate buffer. The column temperature was adjusted to 28° C., the flow rate of the mobile phase to 0.6 μL/min (L means liter), the line speed to 0.86 mm/sec, the pressure to 112 kg/cm$^2$, and the sample was adjusted to a concentration of 1 mg/mL and 1 μL of the sample was injected. The detection was conducted at a position 9 cm away from the column by ultraviolet absorption at 210 nm.

The results in FIG. 3 show that the R-isomer and the S-isomer of 1,1'-bis-2-naphtol were separated.

Comparative Example

An aromatic compound (2-[(4-(1-methyl-1-[4-(2oxiranylmethoxy)phenyl]ethyl)phenoxy)methyl]oxirane: BADE) was used as epoxy compound. Regarding an amine compound and a porogen, BACM and PEG200 were used as the amine compound and as the porogen, respectively, in the same manner as in the example 1.

0.52 g of BACM was dissolved in 7.20 g of PEG200 on heating and then 2.33 g of BADE was added, mixed and stirred. The solution was filled into a fused quartz capillary tube, and heated for 1 hour in an oven at 120° C. to be polymerized.

Then, the resultant was washed with water and methanol, and then dried in vacuo.

Production Conditions

| | |
|---|---|
| BADE | 2.33 g |
| BACM | 0.52 g |
| PEG200 | 7.20 g |
| Temperature | 120° C. |

A separation chromatogram of uracil and benzene obtained by use of the organic polymer monolith capillary column (100 μm in inner diameter and 20 cm in length) of the comparative example produced above is shown in FIG. 4. The mobile phase was a 60% aqueous acetonitrile solution, which was adjusted to pH 7.0 with 20 mM phosphate buffer. The column temperature was adjusted to room temperature, the flow rate of the mobile phase to 0.15 ml/min, the line speed to 1.01 mm/sec, and the pressure to 50 kg/cm$^2$. The detection was conducted with a capillary having an inner diameter of 50 μm placed at a position 9 cm away from the column, by ultraviolet absorption at 210 nm.

In FIG. 4, the earlier peak corresponds to uracil and the latter peak corresponds to benzene. The theoretical plate number determined by the half-value width method is 3,085 for uracil and 378 for benzene, which are not more than 1/10 in comparison to that obtained in the example 1 of the present invention.

This is likely to be because the formed skeletal phase contains aromatic-derived carbon atoms due to the use of an aromatic compound as an epoxy compound.

INDUSTRIAL APPLICABILITY

The monolith separation medium of the present invention can be used as a stationary phase for liquid chromatography, even for general-purpose size columns as well as for capillary columns.

BRIEF DESCRIPTION OF THE DRAWINGS

FIG. 1 A partially sectional view of an organic polymer monolith capillary column produced in one example and a diagram showing a scanning electron microscopic image of an organic polymer monolith in the capillary column.

Figure 2:
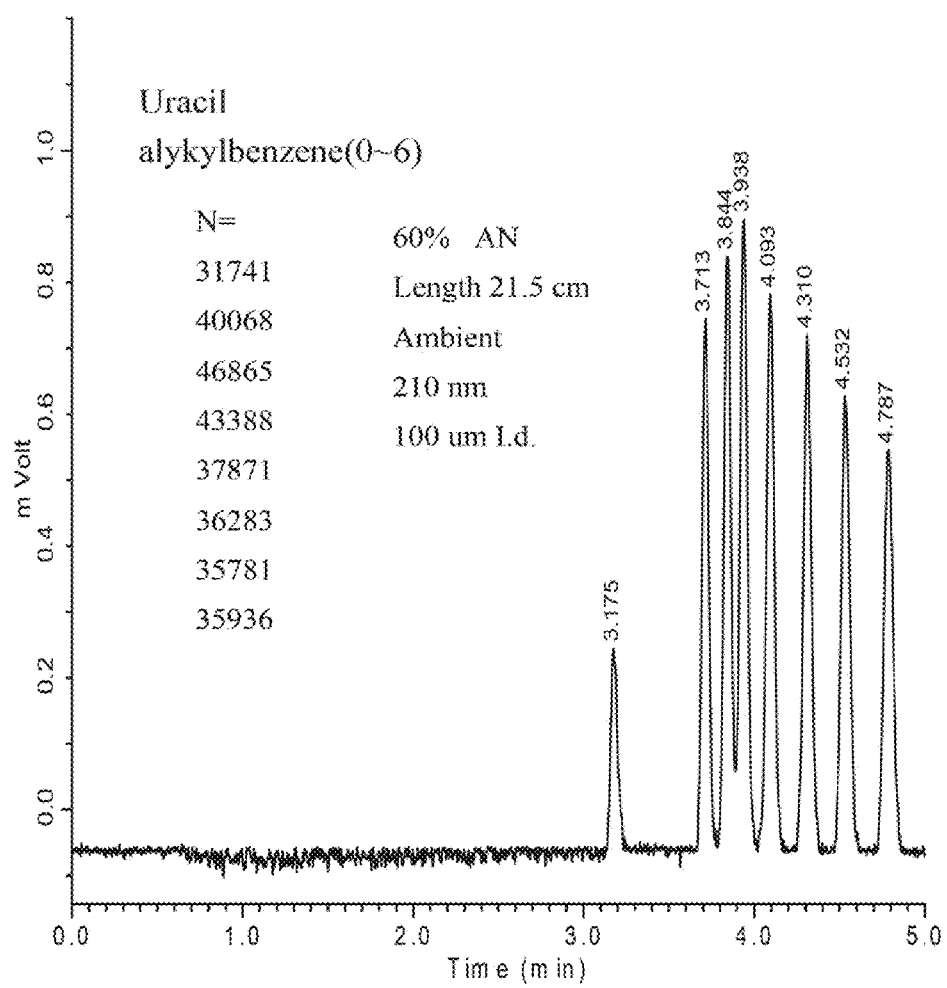
FIG. 2 A separation chromatogram of uracil and alkylbenzenes by the capillary column of the example.
Figure 3:
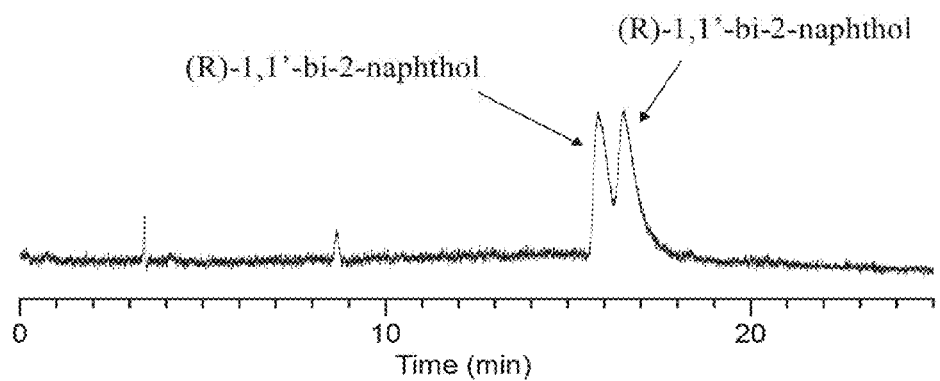
FIG. 3 A separation chromatogram of optical antipodes by an organic polymer monolith capillary column produced in another example.
Figure 4:
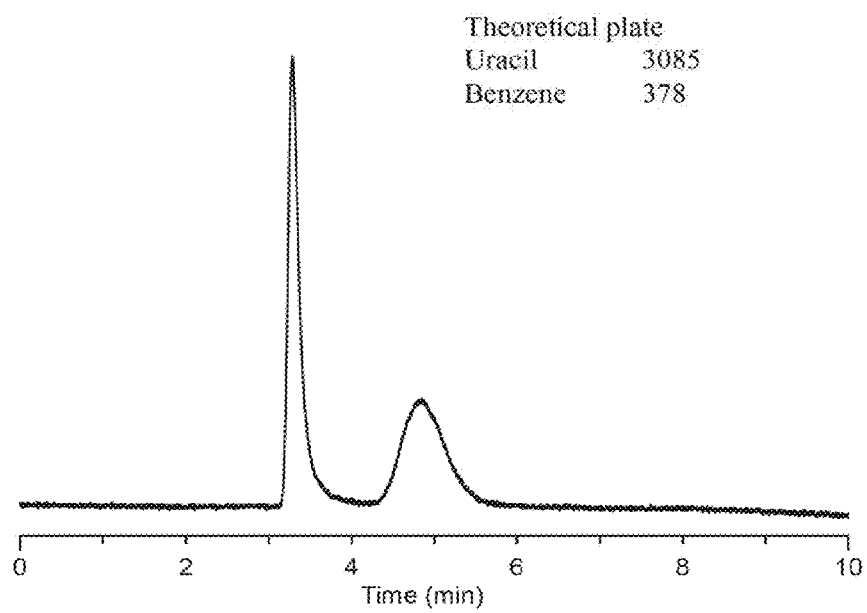
FIG. 4 A separation chromatogram of uracil and benzene by the organic polymer monolith capillary column produced in the comparative example.

What is claimed is:

1. A monolith separation column for chromatography comprising:
   a capillary tube;
   a skeletal phase of an organic macromolecular gel-like monolith formed in the capillary tube;
   a pore formed by the skeletal phase and being continuous in the form of three-dimensional network; and
   a functional group present on the surface of the skeletal phase and permitting introduction of a new functional group,
   wherein the skeletal phase has an average diameter of submicron to micrometer size, has a non-particle-aggregation-type co-continuous structure, is constituted of an addition polymer from 2,2,2-tri-(2,3-epoxypropyl)-isocyanurate as an epoxy compound and an amine compound having two or more amino groups in a molecule, and does not contain any carbon atom constituting an aromatic compound, and
   wherein the monolith separation column is obtained by:
   (A) filling the epoxy compound, the amino compound and a porogen into a capillary tube;
   (B) heating the epoxy compound and the amine compound within a range of from 60 to 200° C. in the porogen to polymerize them to obtain a gel-like material in the capillary tube, and
   (C) then washing the gel-like material with a solvent to remove the porogen to leave the skeletal phase in the capillary tube.

2. The monolith separation column according to claim 1, wherein the separation medium has a theoretical plate number of 50000 or more theoretical plates per meter of column length.

3. The monolith separation column according to claim 1, wherein both the epoxy and amine compounds are optically active substances, and the separation medium has a separation ability for optical antipodes.

4. A process for producing the monolith separation medium according to claim 1, comprising the steps of:
   (A) a step of heating an epoxy compound and an amine compound within a range of from 60 to 200° C. in a porogen to polymerize them to obtain a gel-like material,
   (B) then a step of washing the gel-like material with a solvent to remove the porogen to leave the skeletal phase, and
   (C) then a step of drying,
   wherein the epoxy compound is 2,2,2-tri-(2, 3-epoxypropyl)-isocyanurate,
   wherein the amine compound has two or more amino groups in a molecule, and
   wherein the skeletal phase does not contain any carbon atom constituting an aromatic compound.

5. The process for producing a monolith separation medium according claim 4, wherein optically active substances are used as both the epoxy and amine compounds.

6. The process for producing a monolith separation medium according to claim 4, wherein the porogen is a cellosolve such as methyl cellosolve and ethylcellosolve, an ester such as ethylene glycol monomethyl ether acetate and propylene glycol monomethyl ether acetate, or a glycol such as polyethylene glycol and polypropylene glycol.

7. The process for producing a monolith separation medium according to claim 6, wherein the porogen is polyethylene glycol.

8. The monolith separation column according to claim 1, wherein the amine compound is bis(4-aminocyclohexyl)methane.

9. The monolith separation column according to claim 3, wherein the amine compound is (1S,2S)-(+)-1,2-cyclohexanediamine.

10. The process for producing a monolith separation medium according to claim 4, wherein the amine compound is bis(4-aminocyclohexyl)methane.

11. The process for producing a monolith separation medium according to claim 5, wherein the amine compound is (1S,2S)-(+)-1,2-cyclohexanediamine.

* * * * *